United States Patent [19]

Hu

[11] Patent Number: 5,807,115

[45] Date of Patent: Sep. 15, 1998

[54] DISSOLUTION APPARATUS SIMULATING PHYSIOLOGICAL GASTROINTESTINAL CONDITIONS

[76] Inventor: Oliver Yoa-Pu Hu, No. 18, Sih-Yaun St., Taipei, Taiwan

[21] Appl. No.: 594,595

[22] Filed: Jan. 31, 1996

[51] Int. Cl.$^6$ .................................................. G09B 23/28
[52] U.S. Cl. ........................................................ 434/272
[58] Field of Search .................................. 434/272, 267, 434/262; 73/866, 865.6, 866.5

[56] References Cited

U.S. PATENT DOCUMENTS 4,335,438  6/1982  Smolen ................................... 364/497

Primary Examiner—Jeffrey A. Smith
Attorney, Agent, or Firm—Beveridge, DeGrandi, Weilacher & Young LLP

[57] ABSTRACT

An automated dissolution apparatus and method that simulates the physiological condition of gastrointestinal tract has been developed. The invention is capable of continuously adjusting the pH and enzyme content of dissolution medium with consideration of the transit time of a pharmaceutical dosage form. The apparatus includes a pH meter with recorder, a dissolution tester, a UV spectrophotometer, a dissolution data recorder with processor, a personal computer and a printer. The present invention can adjust the pH and enzyme content of a dissolution medium based on the literature information of human gastrointestinal conditions and transit times of various pharmaceutical dosage forms. Use of the present invention not only can change the pH and enzyme content of dissolution medium continueously, but also can differentiate the change of drug release and effects of pH and enzyme content on the drug release rate of pharmaceutical formulations.

10 Claims, 10 Drawing Sheets

DISSOLUTION APPARATUS SIMULATING PHYSIOLOGICAL GASTROINTESTINAL CONDITIONS

FIELD OF THE INVENTION

This invention is a novel automated dissolution apparatus that simulates the physiological condition of the gastrointestinal tract. The invention is capable of continuously adjusting the pH and enzyme content of dissolution medium with consideration of the transit time of a pharmaceutical dosage form.

BACKGROUND INFORMATION

The development of oral solid dosage forms is important, since solid dosage forms have most advantages of liquid dosage forms. During the development of solid oral dosage forms, in vitro dissolution is often used as a tool to evaluate the release pattern of a formulation. Excipients in the formulation are capable of controlling the release of the active ingredient which is the desired rate limiting step. Since publication of the *United States Pharmacopeia XVIX*, 1975 edition, there is an increasing trend of using in vitro dissolution to predict the bioavailability of the product. The underlying assumption is that in vivo drug release and absorption behavior can be predicted based on the data of in vitro dissolution. For this reason, establishing the correlation of between in vitro dissolution and in vivo absorption data not only assures the absorption quality in the body, but also is a useful basis for the development of other dosage forms. Thus, one of the important technical problems in modern pharmaceutics is to develop an in vitro dissolution method to simulate the real dissolution conditions of a drug in a physiological environment, for such results can offer a reliable correlation between in vitro and in vivo conditions.

In fact, the bioavailability of a drug is quite different from its in vitro dissolution. As shown in FIG. 1, most currently available dissolution methods do not fully simulate the physiological conditions of the human gastrointestinal tract. The pH is especially variable in different sites of the gastrointestinal tract. Other factors, such as the transit time of a pharmaceutical preparation may vary in different sites of gastrointestinal tract illustrated FIG. 2 and Tables I to III, are also important. The change of pH and transit time in different sites of gastrointestinal tract may affect the dissolution and absorption of a pharmaceutical formulation. In summary, developing an apparatus or a method capable of simulating the in vivo drug dissolution is an important issue.

In NF XIII, in vitro dissolutions of timed release tablets and capsules adopt a method of mixing the simulated gastric fluid with the simulated intestinal fluid in different ratios to adjust the pH value of medium. Five levels of pH ranging from 1.2 to 7.5 are used. This procedure is quite complicate and tedious. Moreover, the transit time is not considered. In USP XXII, dissolutions of extended-release and delayed-release dosage forms adopt two stages for changing the pH. The first stage is to place the solid preparation in a 0.1N hydrochloric acid solution for two hours. For the second stage, the solid preparation is transferred to a pH 6.8 buffer for another 45 minutes. This method is simplified, however, two pH levels cannot fully reflect the real physiological conditions in the gastrointestinal tract. Also, the transit time and variable pHs in different sites of the gastrointestinal tract are not considered. In 1980, *J. Pharm. Sci.* volume 69, issue 12, from pages 1388 to 1392, Takenada et al. proposed a flow type apparatus which could change medium continuously. In this method, an alkaline solution is delivered via a pump to the dissolution medium to change the pH, simulating the pH condition of the gastrointestinal tract. The pump delivers alkaline solution at a constant rate, but the delivery is not programmable. There are some other problems for this system, such as the pH levels of the medium do not reflect the real gastrointestinal tract condition, and most important has the transit time is not considered. Also, the operation is not automatically recorded. Backett et al. in J. Pharm. Sci. 80, 10, 991–994 (1991), revealed a Bio-Dis in vitro dissolution apparatus. This method performed dissolution by moving tubes containing the testing drug into other tubes containing medium with a different pH. This type of operation is good for studying effects of various pH on the drug dissolution. However, the change of pH is not continuous, and a maximum of 5 different levels of pH of the medium are allowed. In addition, whenever a pH change is required, the sample has to be transferred to another vessel. This step is not practical since the drug might be already disintegrated at the previous vessel. It is difficult to move an already disintegrated solid sample. Thus, the result of dissolution is often not accurate. This kind of design still does not reflect the actual change of pH and enzyme condition in gastrointestinal tract. In Drug Dev. Ind. Pharm. 14, 4, 5537–5544 (1988), Das et al. adopted a method in which three solutions with different pH levels were combined whenever pH change of the medium was required. This method did not continuously change the pH, and transit time was not considered either. Moreover, the method is tedious and inconvenient, especially for controlled release dosage forms requiring a long time to complete the drug release. Besides the previously mentioned methods, two methods of changing pH of the medium are often used. One method is to place various preparations in different pH solutions. The other method is to transfer preparations from low level pH solutions to high level pH solutions. Results of these two types of dissolutions may be different, and the real change of pH and enzyme condition are not reflected. Thus, an automated dissolution tester is needed to perform a complicated study and to closer reflect the real physiological gastrointestinal conditions. In summary, a dissolution apparatus that is capable of continuously changing the pH and enzyme conditions of the gastrointestinal tract and also reflecting the real physiological gastrointestinal conditions, especially the transit time, has not been developed.

SUMMARY OF THE INVENTION

One aspect of the invention relates to an automated dissolution apparatus which includes: a speed controller, recorders, detectors, a printer, wherein the improvement comprises: the speed controller contains a peristaltic pump, recorders and detectors include a pH meter, a dissolution data recorder and processor (personal computer), a UV spectrophotometer, and a separate dissolution tester. The dissolution data recorder and processor that controls the change of pH or enzymes continuously simulates the real condition of gastrointestinal tract.

In another aspect, the invention relates to a dissolution method simulating the physiological conditions in gastrointestinal tract:

(1) with or without enzyme in simulated gastric fluid and simulated intestinal fluid.

(2) based on human physiological gastrointestinal pH, enzyme content, and drug transit time with changing pH and enzyme content in dissolution media.

(3) with continuous change of pH and enzyme content in the dissolution media.

DESCRIPTION OF THE INVENTION

The present invention is an apparatus capable of simulating drug dissolution under human gastrointestinal tract conditions, with the capability of continuously changing and recording gastrointestinal pH and enzyme conditions based on the transit time of a drug. The whole procedure is automatically monitored.

The present invention consists of the following units: a peristaltic pump speed controller (10), a peristaltic pump (20), a pH meter with recorder (30), a dissolution tester (40), a UV spectrophotometer (50), a printer (60), and a data recorder with processor (70).

The connection of each unit is as follows: the peristaltic pump (20) is connected with the speed controller (10) for controlling flow rate as constant. More than twelve acid-base resistant tubings (21) are connected between the peristaltic pump and the dissolution tester (40) for delivering the dissolution medium to the dissolution vessels (41). The probe of the pH meter (30) is immersed into the dissolution vessels to monitor the change of pH and this change can be recorded and routed to the printer. The dissolution tester (40) is connected to the data recorder with processor (70) and the operation of the dissolution tester is controlled by the processor. The dissolution tester is also connected to the UV spectrophotometer (50). Under the control of processor, automatic sampling is performed at preset intervals, and the dissolution medium is routed to the UV (50) by flow-type delivery. Results of readings are recorded by the recorder and calculated by the processor (70). After calculation, dissolution data are plotted and a printout is obtained from the printer (60). The procedure for adding the G-I enzyme is similar.

[A] Speed controller of peristaltic pump

The speed controller of peristaltic pump (10) is shown in FIG. 3. The main function of the speed controller is to control the flow rate of the peristaltic pump. After connecting the speed controller and peristaltic pump, the operation parameters are entered on the control panel (11) in order to control the flow rate. The following is the explanation of each operation parameter:

"D" refers to delete the setting of a group. By pressing this key, the order of the following group of settings is advanced.

"C" refers to check the setting of a group.

"S" refers to set parameters of each group. Before setting parameters for each group, this key first is pressed.

"T" refers to set the current time, and also for returning to current time while checking the content of each group.

"M" refers to changing the starting and ending time, and flow rate for each group. The order of each group is not advanced.

"E" refers to ending the setting. "C" can be pressed to check the settings of each group.

The control panel (11) of the speed controller (10) allows 24 groups of settings to control the starting time, ending time, and flow rate in accordance to the need of the actual condition. To set the starting time and ending time, several groups of two digits which represent hours, minutes, and seconds, respectively, are keyed in. The flow rate is expressed by 3 digits ranging from 001 to 100. Another way to change flow rate is to replace different sizes of tubings that are capable of delivering fluid ranging from 0.024 ml/min to 20 ml/min. The current time can be set via the panel of speed controller, thus, the starting time can be controlled. For instance, the peristaltic pump can be set to start operation after 1 hour, or after 24 hours. Since 24 groups of settings are allowed, the application of the present invention is flexible. In addition, the timer in the controller (10) is cycled for up to 24 days. Therefore, the flow rate controller for the present invention can control the operation effectively and automatically. The similar program can be built in a personal computer.

Procedures to operate the flow rate controller are as follows:

Operation method (1)—Setting up the current time.

1. Turn on power switch on the peristaltic pump, when screen of speed control shows , press T, the screen then shows only . At this moment, it accepts numbers from 00 to 23. For example, when digits 09 are pressed the screen then shows 9̲ to indicate 9 AM.
2. Upon finishing the setting of the hours, the screen shows , and the digits for minutes are then inputted. It accepts numbers from 00 to 59. The first two digits represent "minutes".
3. To set up seconds, digits 00 to 59 are pressed. After input, they appear as the last two digits. For example, 5906 means 59 minutes and 06 seconds.
4. When hours, minutes, and seconds are set, the E key is pressed and the screen then shows the current time of hours and minutes.

Operation method (2)—Setting of the starting time, stopping time, and flow rate

1. Before setting, the S key is pressed once, the screen then shows . To set the hour, the numbers then appear in the first two digits from the left, then when setting the minutes, the numbers appear in the right two digits. This is the starting time.
2. At that moment, the screen shows again and the previous steps are followed to set the ending time.
3. When the starting time and the ending time are set, the screen shows , and the flow rate can be set. The range of settings for the flow rate is from 100.0 to 1.0%. For example, when setting 25% speed, digits 0250 are pressed. For 100% flow rate, press digits 1000. For 1%, 0100 are pressed.
4. When the flow rate is set, E is pressed. This ends the setting of the first group of operational parameters. To set the second group of settings, the S key is again pressed, and the previous steps are followed to complete the setting.
5. A total of 24 groups of operational parameters can be set.

Operation method (3)—Check, change, and delete the setting of each group

1. The setting of a group is checked by pressing the C key, when screen shows 01, this refers to group 1, the screen then shows the starting next. The E key is pressed and the screen shows the ending time. The E key is pressed again and the screen shows the flow rate. The E key is pressed again and the next group setting is shown. After the last group is shown, the screen goes back to the current time.
2. The T key is pressed to stop checking at any time.
3. To change the setting for any group, the M key is pressed after the flow rate is shown. Then the starting time, ending time, and flow rate are set. The E key is pressed to end the setting. The change will not affect other groups of setting.
4. To delete a group of settings, the D key is pressed. The order of next group of setting will advance.

5. If the T key was pressed accidentally, the screen would show on the right side, and the D key is pressed to delete.

Setting for special function (4)—Simulation of the pH change of gastrointestinal tract The present invention is capable of continuously changing gastrointestinal pH and enzyme conditions in accordance to the real physiological condition at different sites of the gastrointestinal tract, and also matching the transit time of various dosage forms. Dissolution media selected for the present invention are simulated gastric fluid and simulated intestinal fluid in USP XXII. The apparatus first delivers simulated gastric fluid, with or without enzyme, to dissolution vessels in accordance to the pH and enzyme conditions of each section of gastrointestinal tract, as shown it FIG. 1. Then simulated intestinal fluid, with or without enzyme, is delivered continuously to vessels containing simulated gastric fluid, based on the drug transit time, pH and enzyme conditions of the gastrointestinal tract. Thus, the condition of drug dissolution in the human gastrointestinal tract is precisely simulated. This system provides a prompt and convenient way to test a formulation design, and study effects of pH on drug release rate and on the amount of dissolution.

As described above, the rate of adding simulated intestinal fluid (with or without enzyme) to simulated gastric fluid (with or without enzyme) ranges from 1% to 100%. The volume of simulated gastric fluid used ranges from 99 ml to 1500 ml. The pH of simulated gastric fluid (with or without enzyme) is between 1 to 3. The volume of simulated intestinal fluid used is ranged from 300 ml to 2000 ml. The pH value of simulated intestinal fluid is ranged from 7 to 9. The concentration of pepsin in the gastric fluid ranges from 1 mg/ml to 5 mg/ml. The concentration of pancreatin in the simulated intestinal fluid ranges from 5 mg/ml to 15 mg/ml. The simulated gastric fluid or intestinal fluid may contain 0.1 to 50% of surfactant, such as sodium lauryl sulfate.

[B] peristaltic pump (See FIG. 3 item 20)

The peristaltic pump includes 12 tubes for delivery. The flow rate is controlled by the speed controller. It delivers dissolution medium via acid and alkaline resistant tubing to dissolution vessels. The diameter of the tubing can be selected in accordance to the practical needs. The diameter of tubing allows fluid delivery ranging from 0.01 ml/min to 20 ml/min.

[C] pH meter with recorder (See FIG. 3 item 30)

The pH meter can monitor the pH change in dissolution vessels. The function of recording time is pre-programmable. The pH meter is fully automatic. The pH meter or the pH probe can be directly connected to the personal computer.

[D] Dissolution tester (See FIG. 3 item 40)

The dissolution tester includes six vessels, the dissolution data recorder is controlled by the processor and programs. The operational temperature and speed are controlled by the processor. The method of sampling is flow-type and can be done at preset intervals. The absorbance is read by the UV spectrophotometer (See FIG. 3 item 50). Results are stored and calculated automatically in the recorder and processor. Printouts of data and dissolution curve can be obtained by the printer.

By employing the present invention, the change of pH is continuous and can be programmed in accordance to different situations for various dosage forms. In the mean time, this invention employs the combination of simulated gastric fluid and simulated intestinal fluid, with consideration of the transit time of various dosage forms, different pH and enzyme contents at different sites of gastrointestinal tract, to simulate the real condition of drug dissolution in human gastrointestinal tracts. This invention is convenient and time-saving.

As described above, the peristaltic pump is a programmable device, which includes the following features:

(1) can set up current time—hour, minutes, seconds.

(2) can set up the starting and ending time of peristaltic pump (hours, minutes).

(3) can set up the rate change during each run.

(4) can modify and check preset values.

(5) can set up at least 24 groups of programs.

(6) the change of flow rate is between 1% to 100%.

The chart of operation is shown as follows:

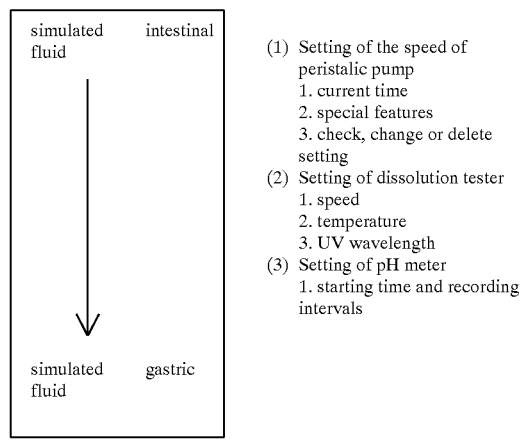

(1) Setting of the speed of peristalic pump
   1. current time
   2. special features
   3. check, change or delete setting
(2) Setting of dissolution tester
   1. speed
   2. temperature
   3. UV wavelength
(3) Setting of pH meter
   1. starting time and recording intervals

BRIEF DESCRIPTION OF THE DRAWINGS

Table I. Gastric retention time of tablets.

Table II. Gastrointestinal transit time of tablets.

Table III. Gastrointestinal transit time of various dosage forms.

Figure 1:
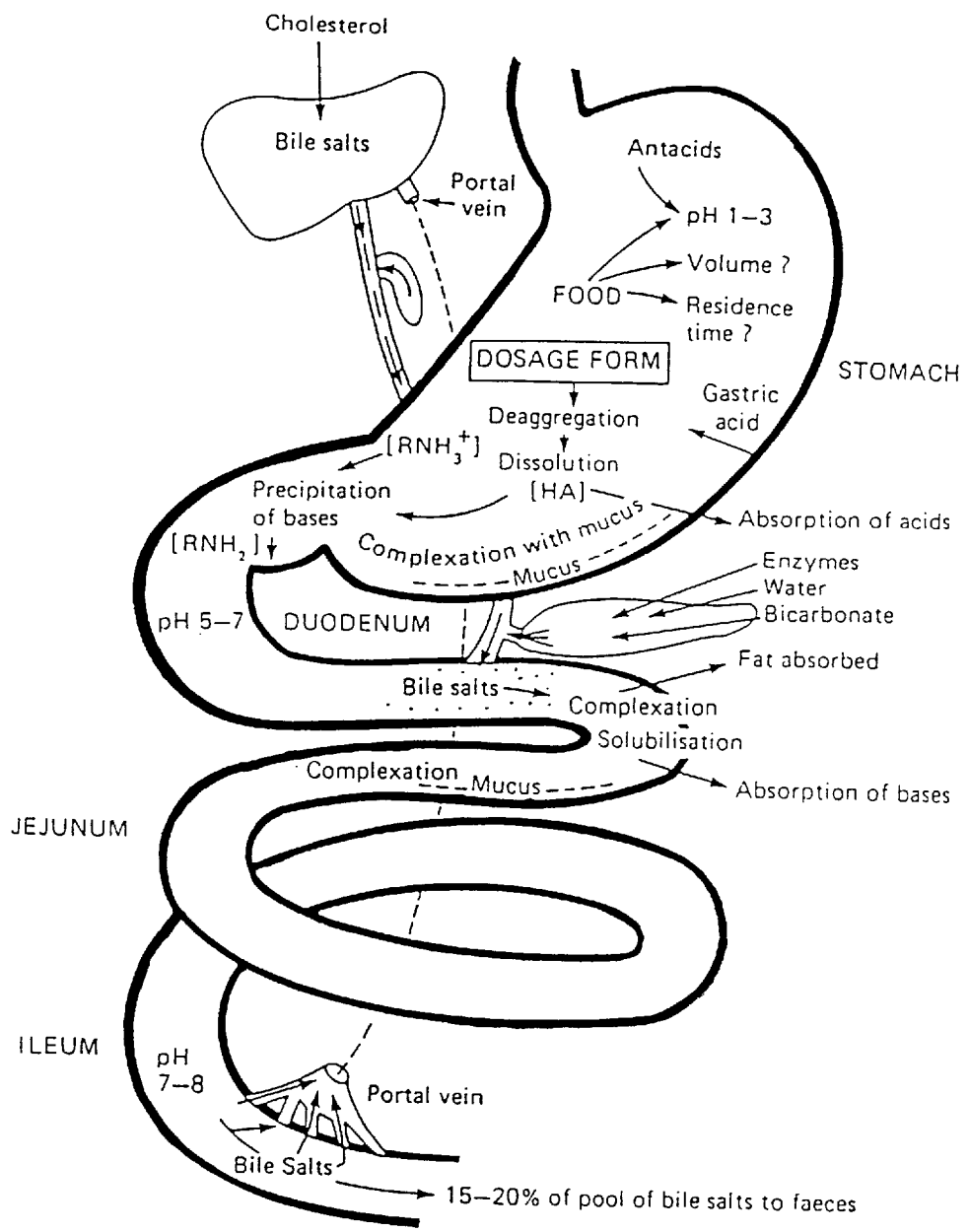

FIG. 1. The pH changes in different sites of human physiological gastrointestinal environment.

Figure 2:
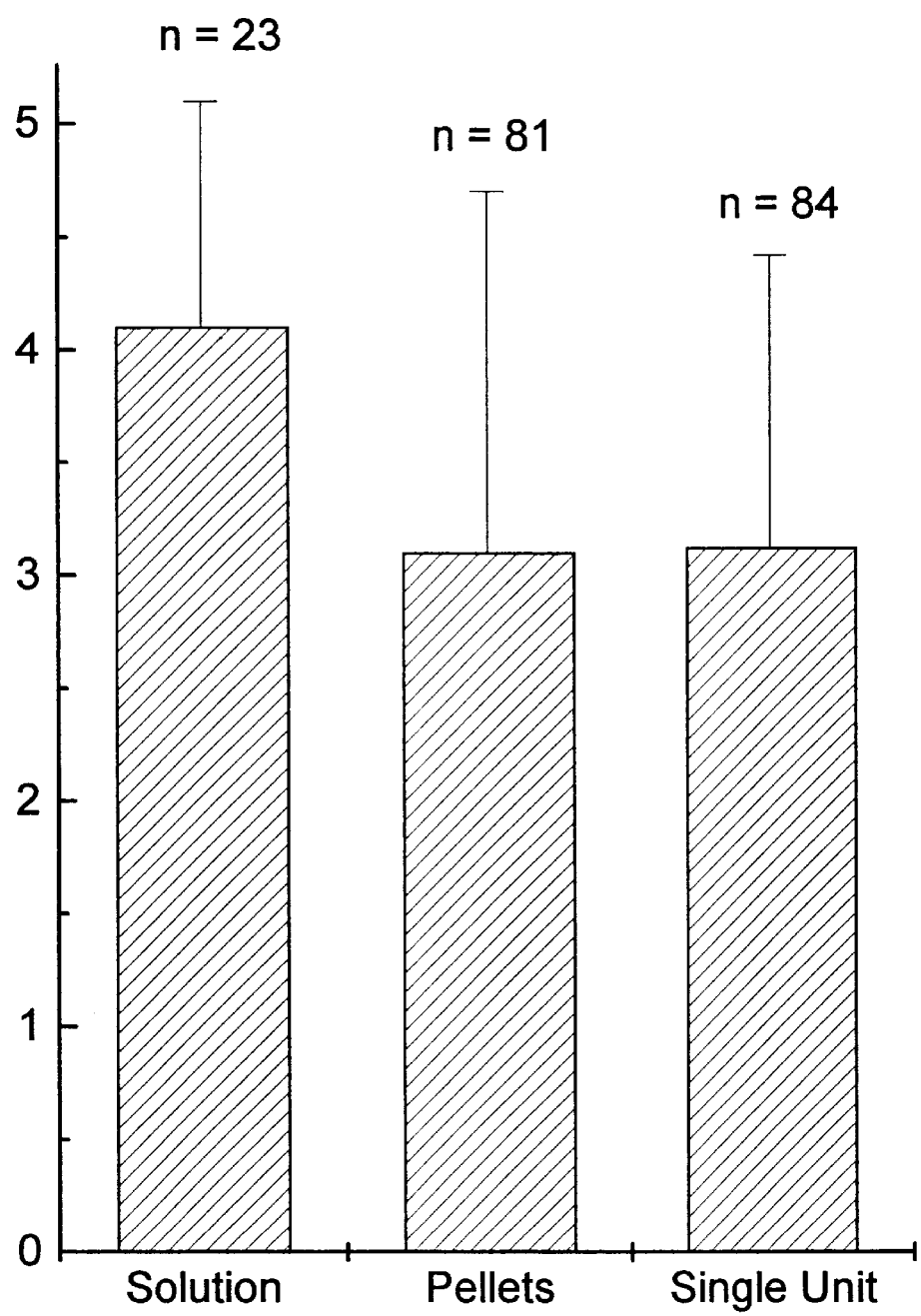

FIG. 2. Small intestinal transit of pharmaceutical dosage forms.

Figure 3:
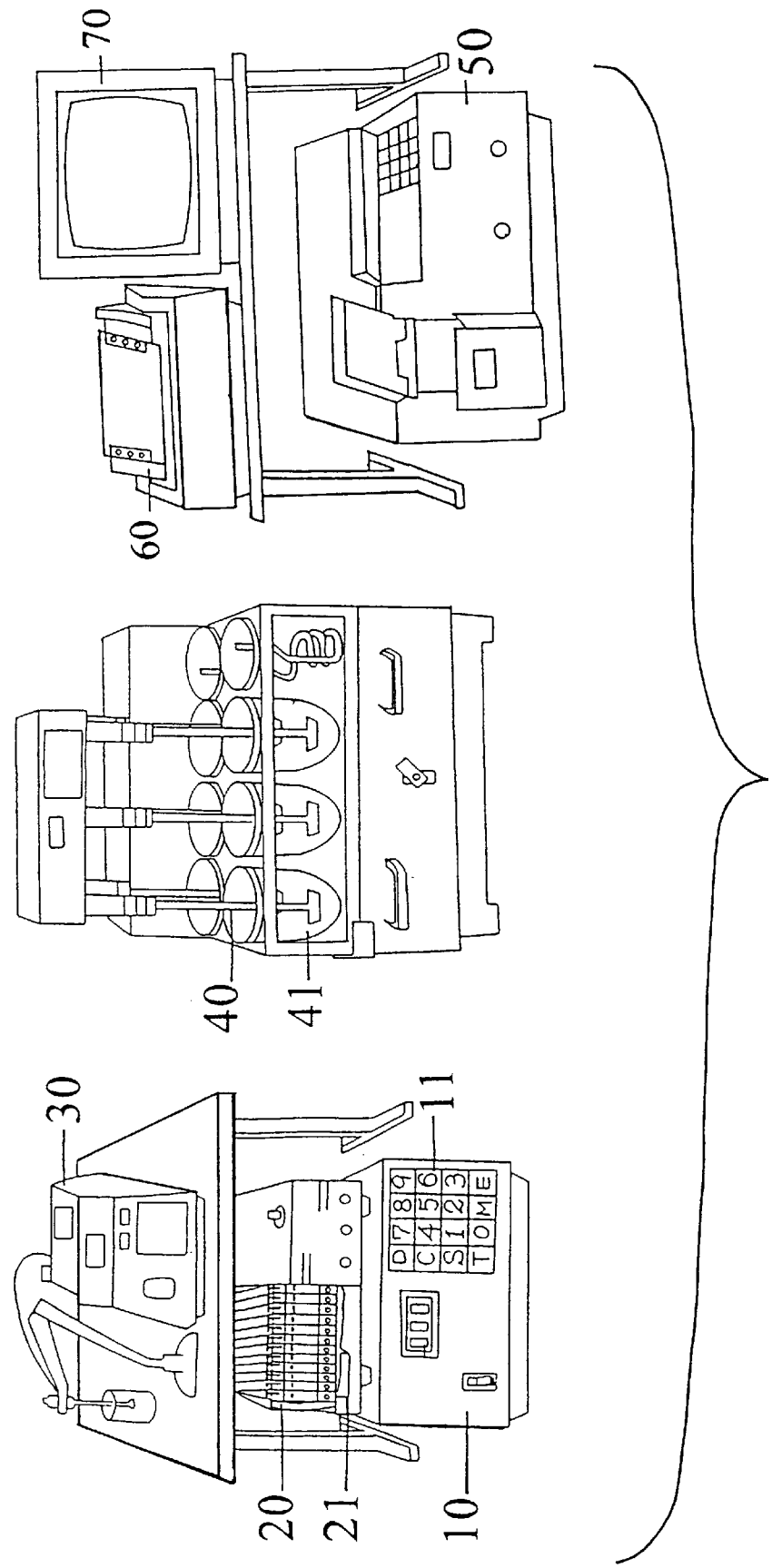

FIG. 3. Automatic in vitro apparatus for simulation of gastrointestinal environments.

Figure 4:
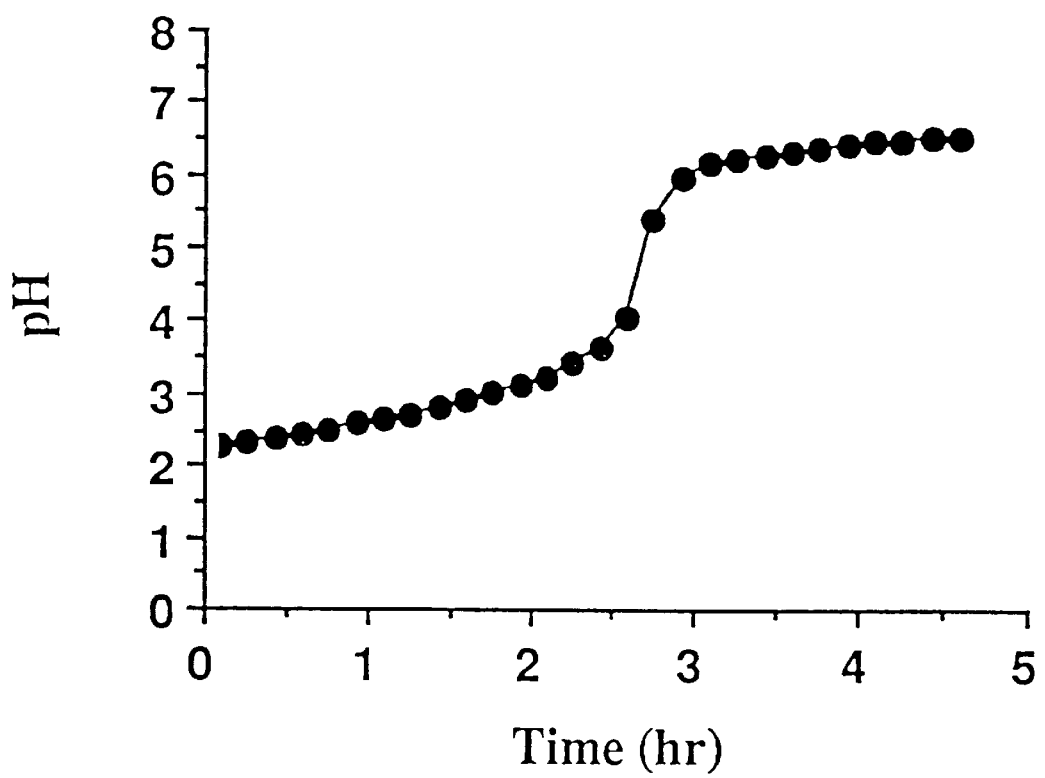

FIG. 4. The change of pH-time profiles of tablets in simulated physiological gastrointestinal environment where pH values were continuously changed.

Figure 5:
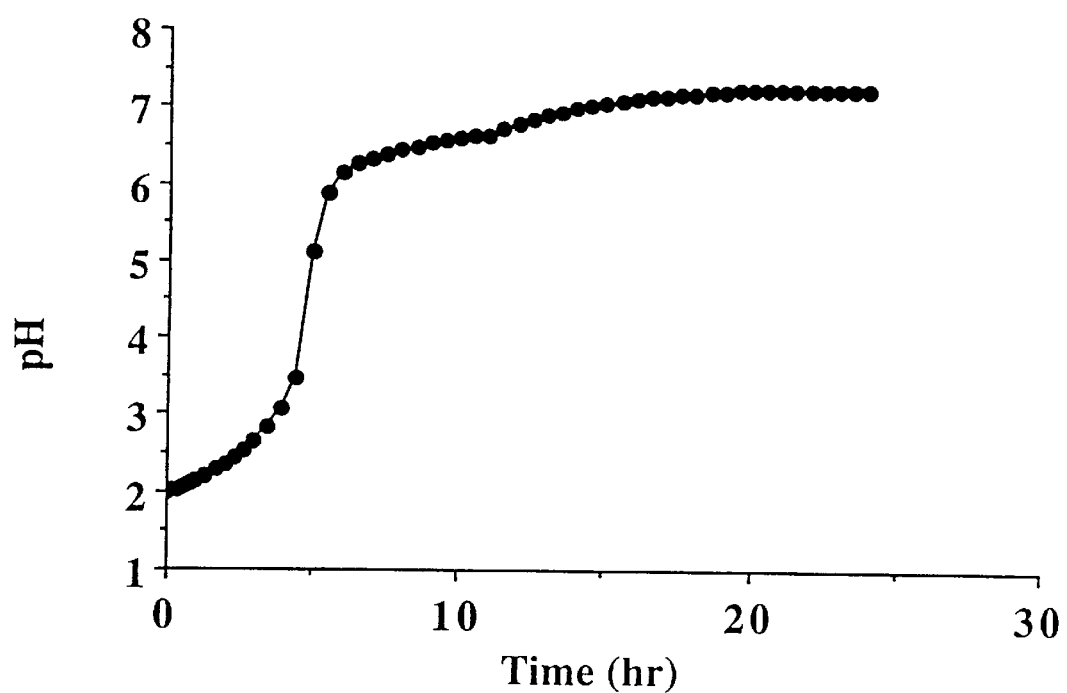

FIG. 5. The change of pH-time profiles of pellets in simulated physiological gastrointestinal environment where pH values were continuously changed.

Figure 6:
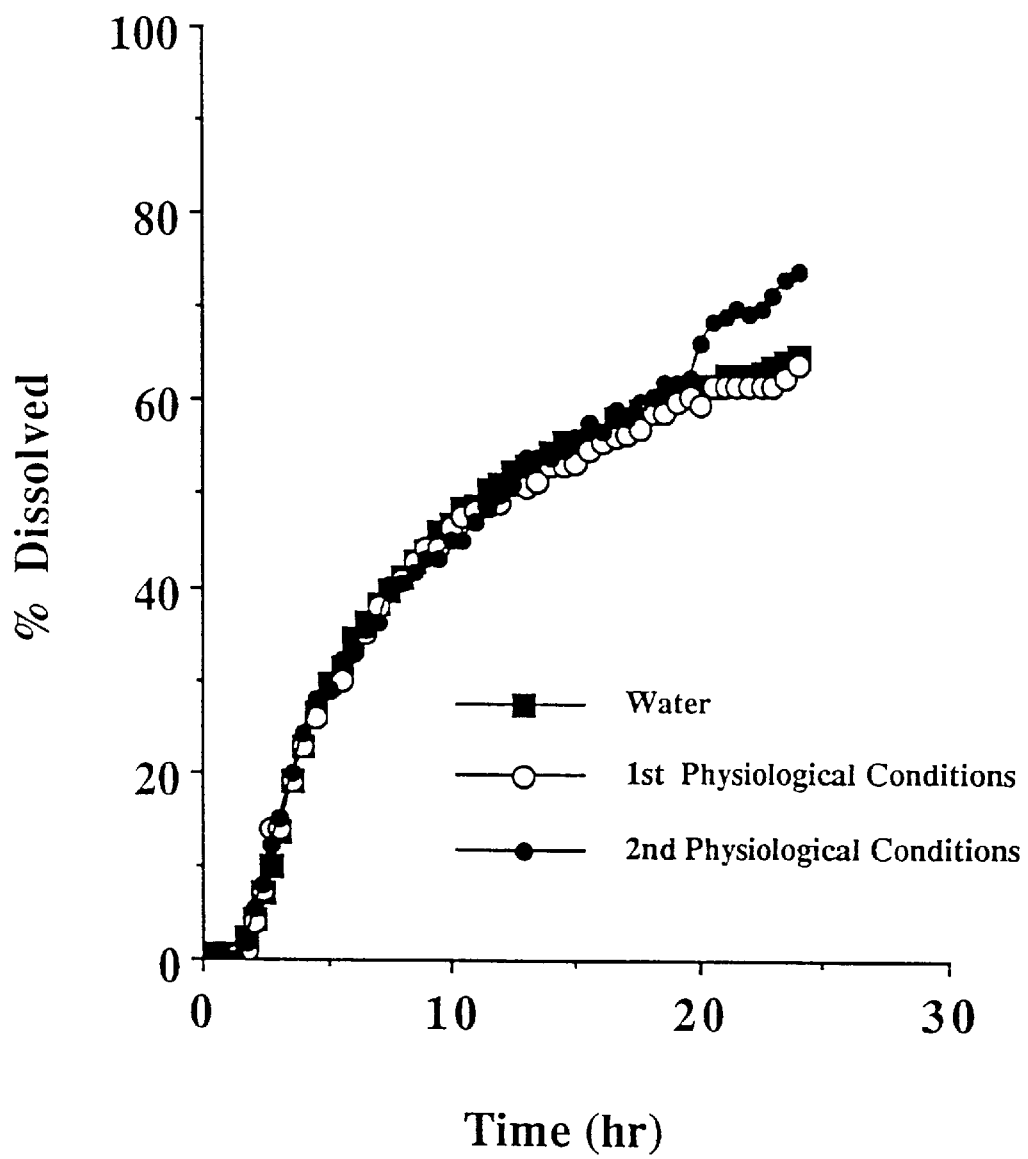

FIG. 6. Dissolution of chlorpheniramine controlled release pellets in water and simulated physiological gastrointestinal environment where pH values were continuously changed.

Figure 7:
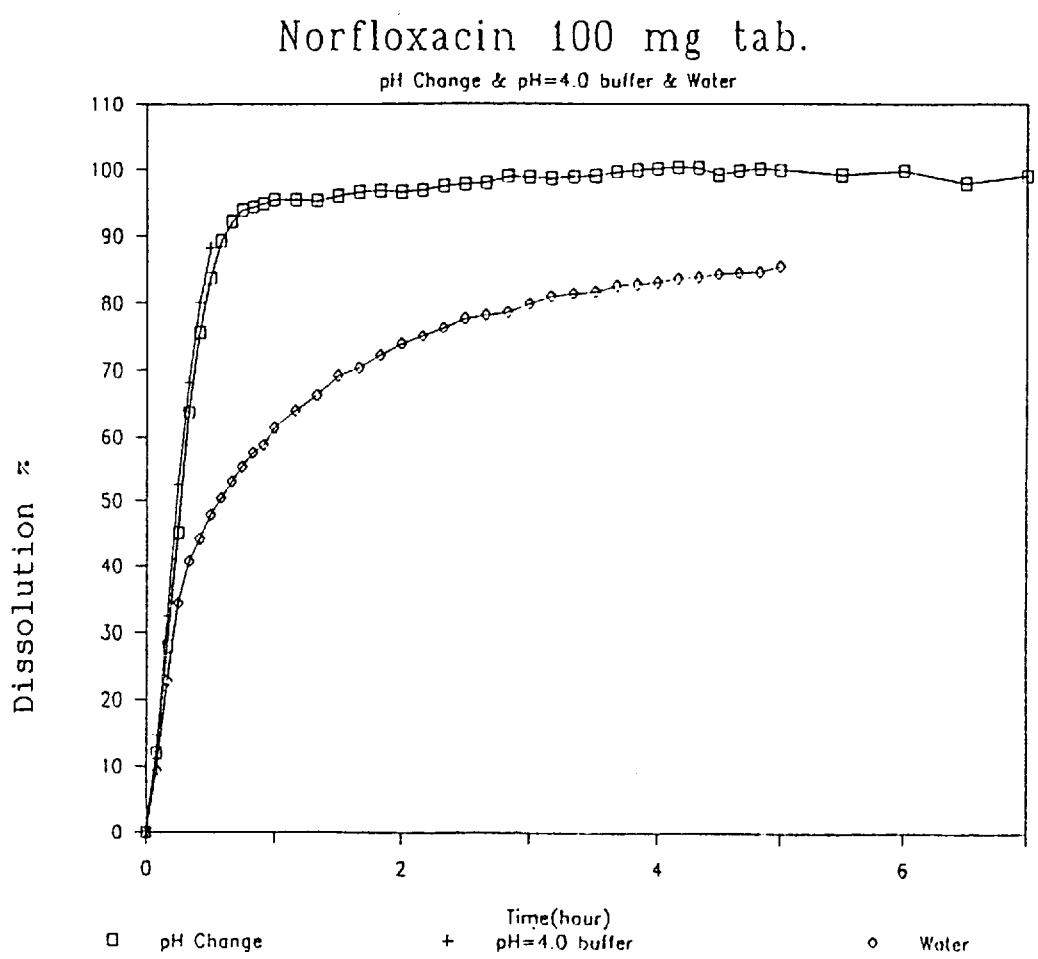

FIG. 7. Dissolution of coated Norfloxacin in water, in pH 4.0 acetate buffer (USP XXII) and in simulated physiological gastrointestinal environment.

Figure 8:
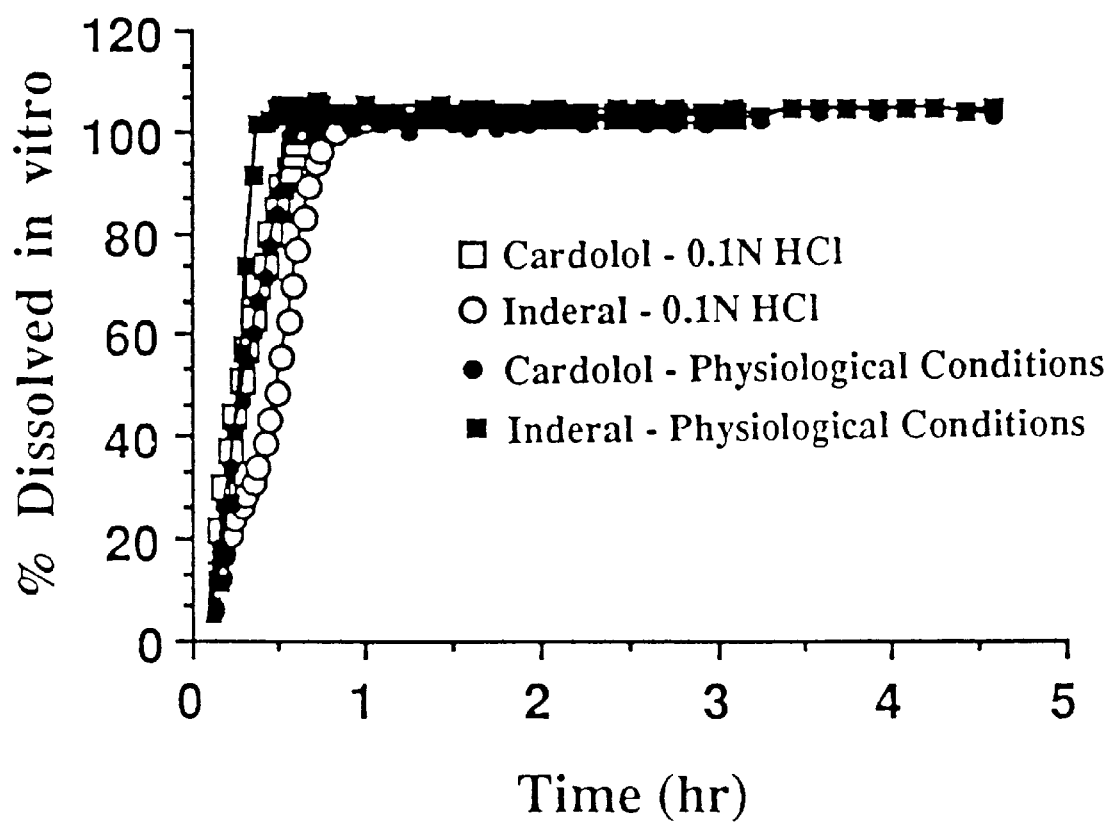

FIG. 8. Dissolutions of CARDOLOL® and INDERAL® tablets in diluted hydrochloric acid and in simulated physiological gastrointestinal environment.

Figure 9:
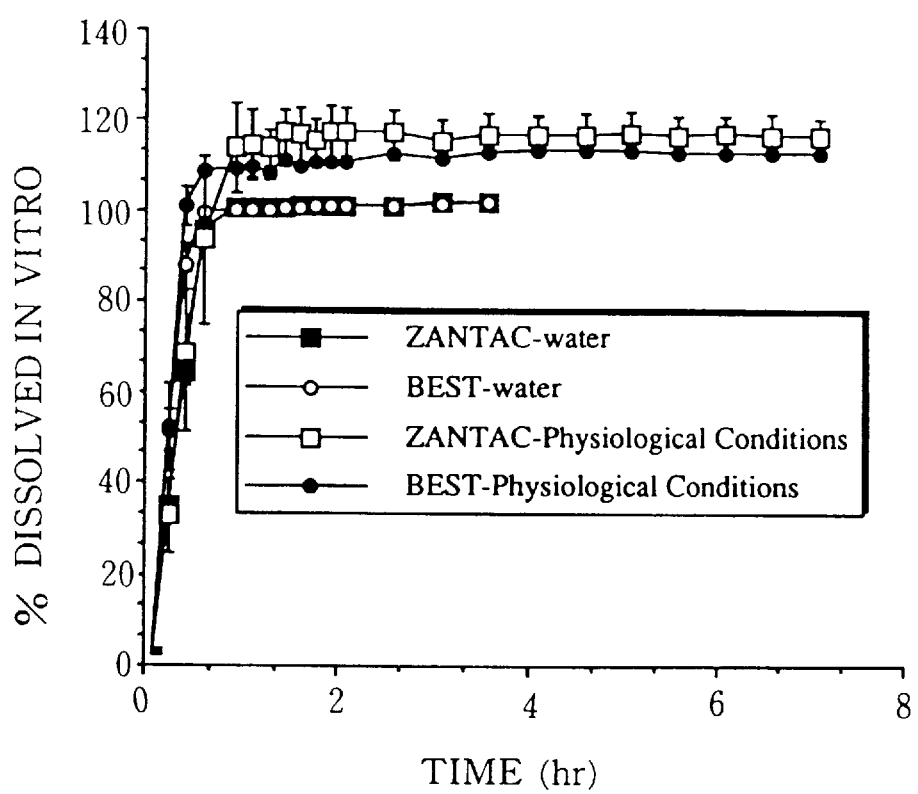

FIG. 9. Percentage vs. time dissolution profiles of ZANTAC® and BEST® in water and in simulated physiological gastrointestinal environment.

Figure 10:
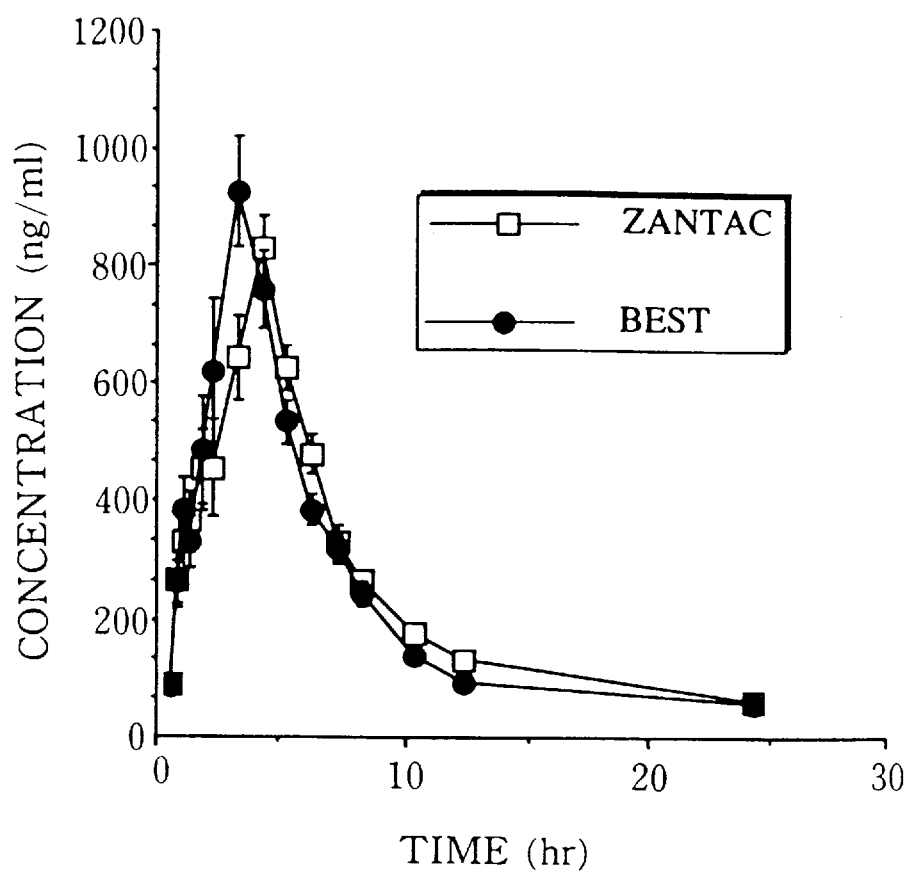

FIG. 10. Blood concentrations vs. time profiles of two Randitidine formulations in 12 healthy volunteers.

DETAILED DESCRIPTION

In order to illustrate the proposed purposes, methods and advantages of this invention more obviously, the following implemented examples are stated concretely, but the extents of this invention are not limited by its contents and conclusions.

EXAMPLE 1

Procedures of setting peristalsis pump
(1) setting the current time: e.g. the present time is 10 AM 30 minutes 20 seconds
turn the power on, then screen shows
press T key, the screen shows press digits 10, the screen shows 1 0 press digits 3020,
press E key, the screen shows 1 0 3 0, this refers to hour and minutes.
(2) setting the speed of peristalsis pump
assuming the setting of the following are needed:

| group | starting time | ending time | speed |
|-------|---------------|-------------|-------|
| 1     | 1200          | 1500        | 60%   |
| 2     | 1500          | 1730        | 25%   | press S key, the screen shows , press digits 1200 the screen shows 1 2 0 0, press digits 1500 the screen shows 1 5 0 0, press digits 0600
press E key, then the first group of setting is done.
press S key, the screen shows , press digits 1500 the screen shows 1 5 0 0, press digits 1730 the screen shows 1 7 3 0, press digits 0250
press E key, then the second group of setting is done.
The controller can accommodate 24 groups of settings.
(3) Checking settings of each group
Press C key, the screen shows 0 1, this indicates the data of first group. Then the screen shows 1 2 0 0, this indicates the starting time of the first group.
Press E key again, the screen shows 1 5 0 0, this indicates the ending time of the first group.
Press E key again, the screen shows 0 6 0 0, this indicates the flow rate of the first group.
Press E key again, the screen shows 0 2, this indicates the data of the second group.
Press E key again, the screen shows 1 6 0 0, this indicates the starting time of the second group.
Press E key again, the screen shows 1 7 3 0, this indicates the ending time of the first group.
Press E key again, the screen shows 0 2 5 0, this indicates the flow rate of the first group.
(4) Change settings of each group
Assuming the starting time of the first group to 1130 is wrong, ending time is correct, and speed is needed to change to 70%, to make change after checking the speed of flow rate in the first group, for the present example is 0 6 0 0,
press M key, the screen shows , press digits 1130 the screen shows , press digits 1500 the screen shows , press digits 0700
press E key to end the change.
To change the second group of settings, wait until flow rate is shown, for the present example is 0 2 5 0, repeat the previous steps. Similarly, to delete the group, press D key after screen shows the flow rate.

Upon finishing previous steps, settings of the present example have been changed to the followings:
The current time is 10 AM 30 minutes 20 seconds

| group | starting time | ending time | speed |
|-------|---------------|-------------|-------|
| 1     | 1130          | 1500        | 70%   |
| 2     | 1500          | 1730        | 25%   |

These new settings indicate that the peristaltic pump is going to start after 1 hour, the maximum flow rate in the first stage is 70% for three and a half hours. In the second stage, the maximum flow rate is 25% for two and a half hours, the simulated intestinal fluid is delivered to the simulated gastric fluid in vessels.

EXAMPLE 2

Schedule and settings in dissolution of propranolol tablet in conditions simulating the pH change of the gastrointestinal tract.

Based on the absorption data and in vitro dissolution time of propranolol tablet, with consideration of the transit time, the operational speed and time of the peristalsis pump was determined as follows:

| group | starting time | ending time | speed |
|-------|---------------|-------------|-------|
| 1     | 1200          | 1500        | 0600  |
| 2     | 1500          | 1630        | 0200  |

Based on the above setting, the simulated intestinal fluid was added to the simulated gastric fluid to simulate the pH change in gastrointestinal tract. Regarding the time setting, the first two digits referred to "hour", the last two digits referred to "minutes", the flow rate was expressed by percentage of the maximum speed, e.g. 0 6 0 0 refers to 60% of the maximum speed. If the peristaltic pump started operation at 12 noon, simulated intestinal fluid at 60% of the maximum rate was delivered to simulated gastric acid for 3 hours. By 3 PM, the flow rate of peristaltic pump was changed to 20% of the maximum rate for 90 minutes, then stopped. Results were shown in FIG. 4, pH values and data were recorded at 10 minute interval.

EXAMPLE 3

Schedule and settings in dissolution of controlled release chlorpheniramine maleate pellets and profiles of pH change in conditions simulating gastrointestinal tract Based on the absorption data and in vitro dissolution time of controlled release chlorpheniramine maleate pellets, with consideration of the transit time, the operational speed and time of the peristalsis pump was determined as follows:

| group | starting time | ending time | speed |
|-------|---------------|-------------|-------|
| 1     | 1645          | 2245        | 0300  |
| 2     | 2245          | 0345        | 0150  |
| 3     | 0345          | 1300        | 0600  |

The simulated intestinal fluid was added to the simulated gastric fluid based on the above setting, to simulate the pH change in gastrointestinal tract. Results are shown in FIG. 5, parameters of settings were shown as above. The result indicates the present invention is capable of changing pH of the medium continuously for at least 22 hours.

EXAMPLE 4

Dissolutions of drugs in simulated gastrointestinal fluid

In the following examples, dissolutions of several drugs were performed by employing the present invention. Simulated intestinal fluid was added to simulated gastric fluid to change the pH of medium with consideration of drug transit time. Based on USP XXII (N=6), 500 ml of simulated gastric fluid was used, temperature was set to 37° C. Samples were collected automatically at fixed intervals and absorbencies were read by a UV spectrophotometer. Readings were compared to reference standards, the percentage of dissolution rate is plotted for the purpose of evaluation of dissolutions.

(1) Dissolution of chlorpheniramine maleate controlled release pellets

Based on the change of pH in physiological condition of gastrointestinal tract, dissolution of chlorpheniramine pellets simulating gastrointestinal environment was performed at stirring speed of 50 rpm, absorbance was read at UV wavelength of 262 nm. The setting of pump speed was shown in Example 3. The dissolution was carried on over 24 hours, and was repeated once. Results are shown in FIG. 6. The dissolution of chlorpheniramine pellets in water was similar to that in simulated gastrointestinal fluid. That is, the dissolution of chlorpheniramine pellets is not affected by the change of pH values. This is very important for a controlled-release preparation. In the mean time, The dissolution curve of the repeated dissolution was almost overlapping the first one, indicating a good reproducibility of the present invention.

(2) Dissolution of norfloxacin tablets

Norfloxacin is a broad-spectrum antibiotic. The dissolution was performed at pH 4.0 acetate buffer in accordance to the requirement in USP XXIII. Additional dissolutions were performed in water and simulated gastrointestinal environment. The speed of stirring was 50 rpm, the UV wavelength was set at 313 nm. The pH change in the simulated gastrointestinal environment is shown in FIG. 4, and results of dissolutions were shown in FIG. 7. The result indicated the dissolution of such tablet in water was lower than that in other media. But dissolution in pH 4.0 acetate buffer was similar to that of simulated gastrointestinal environment. The dissolution of the passed the USP XXIII requirement of releasing more than 80% in 30 minutes. From these results, the dissolution data indicates norfloxacin tablets presents different dissolution in different pH environment.

(3) Dissolution of propranolol tablet

Propranolol is a β receptor blocker. The clinical use is for the treatment of hypertension, cardiac arrhythmia. Two different brands of propranolol tablets were used: CARDOLOL® and INDERAL®. To study the dissolution in simulated pH environment in gastrointestinal tract, together with considering the transit time, the setting of speed of peristalsis pump was the same as shown in example 2, the speed of stirring was 100 rpm, the UV wavelength was set at 365 nm for 0.1N hydrochloric acid solution, and 290 nm for simulated gastrointestinal fluid. Results shown in FIG. 8 indicate the pH of dissolution medium had no effect on CARDOLOL®. However, dissolution of INDERAL® in simulated gastrointestinal fluid was faster than that in 0.1N hydrochloric solution. Thus, dissolution of CARDOLOL® is pH independent, and dissolution of INDERAL® is affected by the change of pH values.

(4) Dissolution of ranitidine

Ranitidine is a $H_2$ blocker. The clinical use is to treat duodenal ulcer and gastric ulcer. Two different brands of ranitidine were selected for dissolution tests. The settings in the simulated gastrointestinal environment were the same as shown in example 2. The speed of stirring was 100 rpm, and the wavelength for the UV detector was set to 280 nm. Results are shown in FIG. 9. The results showed that BEST® and ZANTAC® had almost identical dissolution rates in water, but had different rates in simulated gastrointestinal fluid environment. For both brands, their dissolution rates were affected by the change of pH. However, the dissolution of BEST® was faster than that of ZANTAC®. The blood concentration profile of volunteers as shown in FIG. 10 also indicate the absorption of BEST® was faster than ZANTAC®. This result had good agreement with dissolution data obtained in the simulated gastrointestinal environment. The result indicated that dissolution methods employing the present invention produced better data for in vitro and in vivo correlations.

From results of these experiments, the present invention has been proven to be a simple, automatically operable, and programmable apparatus. It simulates the real condition in human gastrointestinal environment. Factors such as pH change or enzyme content, and drug transit time are also considered while the pump delivering simulates intestinal fluid to simulated gastric fluid. The present invention not only can study the effect of pH on drug release of pharmaceutical formulations in the simulated physiological gastrointestinal conditions, but also can reflect the correlation between dissolution and absorption. It can be a useful tool for establishing the correlation between in vitro and in vivo behavior of a drug.

TABLE I

| | Gastric retention time of tablets. | | | |
|---|---|---|---|---|
| | Dosage Forms Tablets State | | | |
| | Fasted | | Fed | |
| Authors | Floating (Mean ± SE) | Non-float. (Mean ± SE) | Floating (Mean ± SE) | Non-float. (Mean ± SE) |
| Sangekar et al. (1987) | 132 ± 42 (8) | 152 ± 46 (8) | 406 ± 38 (8) | 376 ± 37 (8) |

Floating Tablet' Specific Gravity: 0.96
Non-floating Tablet' Specific Gravity: 1.59

TABLE II

| | Gastrointestinal transit time of tablets. | | | | |
|---|---|---|---|---|---|
| | Dosage Forms Tablets Transit Time | | | | |
| | G. E. T. (min) (Mean ± SE) | | S. T. T. (min) (Mean ± SE) | | |
| Authors | Elderly | Young | Elderly | Young | State |
| Davis et al. (1986) | 52 ± 13 (6) | 38 ± 7 (6) | 198 ± 44 (6) | 180 ± 30 (6) | Fasted |
| | 198 ± 49 (6) | 180 ± 72 (6) | 204 ± 33 (6) | 192 ± 33 (6) | Fed L.B.K. |

G.E.T.: Gastric Emptying Time.
S.T.T.: Small Intestinal Transit Time.
L.B.K.: Light Breakfast.

TABLE III

Gastrointestinal transit time of various dosage forms.

| | Pellets (T50%) | | Tablets | | Solution (T50%) | | |
|---|---|---|---|---|---|---|---|
| | \multicolumn{6}{c|}{Transit Time} | |
| Authors | G. E. T. (min) (Mean ± SE) | S. T. T. (min) (Mean ± SE) | G. E. T. (min) (Mean ± SE) | S. T. T. (min) (Mean ± SE) | G. E. T. (min) (Mean ± SE) | S. T. T. (min) (Mean ± SE) | State |
| Davis et al. (1984) | 99 ± 20 (6) | 227 ± 82 (5) | 164 ± 92 (6) | 188 ± 23 (5) | | | L.K.B. |
| Davis et al. (1984) | 119 ± 15 (6) | 188 ± 28 (6) | 183 ± 77 (5) | 191 ± 24 (5) | | | L.K.B. |
| | 285 ± 45 (6) | 202 ± 28 (6) | >500 (6) | <1400 (6) | | | H.K.B. |
| Christensen et al.(1985) | 99 ± 7 (6) | 204 ± 37 (6) | | | 18 ± 4 (6) | 246 ± 28 (6) | L.K.B. |
| Davis et al. (1987) | 78 ± 8 (6) | 176 ± 16 (6) | | | | | L.K.B. |
| | 170 ± 11 (6) | 250 ± 42 (6) | | | | | H.K.B. |

G.E.T.: Gastric Emptying Time (min).
S.T.T.: Small Intestinal Transit Time (min).
L.B.K.: Light Breakfast.
H.B.K.: Heavy Breakfast.

What is claimed it:

1. An automated apparatus for measuring the rate of dissolution of a drug dosage form comprising:

a dissolution vessel, delivery means for delivering into the dissolution vessel a dissolution media comprising at least a first gastrointestinal enzyme, means for controlling the delivery means in a manner so as to simulate, within the dissolution vessel, the time dependent physiological conditions encountered by a drug dosage form during transit through a gastrointestinal tract, means for measuring pH of the dissolution media within the dissolution vessel, and dissolution measuring means for measuring the extent of dissolution of the drug dosage form within the dissolution vessel.

2. The automated dissolution apparatus of claim 1 wherein the dissolution media further includes a simulated gastric fluid and a simulated intestinal fluid.

3. The automated dissolution apparatus of claim 2 wherein the simulated gastric fluid has a pH of from about 1 to about 3 and the simulated intestinal fluid has a pH of from about 7 to about 9.

4. The automated dissolution apparatus of claim 3 wherein the dissolution measuring means is an UV spectrophotometer.

5. The automated dissolution apparatus of claim 3 wherein the pH measurement and the drug dosage form dissolution measurement are conducted continuously.

6. The automated dissolution apparatus of claim 2 wherein the dissolution media further includes a second gastrointestinal enzyme.

7. The automated dissolution apparatus of claim 6 wherein the first gastrointestinal enzyme is pepsin.

8. The automated dissolution apparatus of claim 7 wherein the second gastrointestinal enzyme is pancreatin.

9. The automated dissolution apparatus of claim 7 that is capable of making drug dosage form measurements on at least 6 drug dosage form samples.

10. The automated dissolution apparatus of claim 1 further comprising:

means for recording the pH measurement and the extent of dissolution measurement.

* * * * *